United States Patent
Zalit et al.

(10) Patent No.: US 8,367,106 B2
(45) Date of Patent: *Feb. 5, 2013

(54) COMPRESSED SOLID DOSAGE FORM MANUFACTURING PROCESS WELL-SUITED FOR USE WITH DRUGS OF LOW AQUEOUS SOLUBILITY AND COMPRESSED SOLID DOSAGE FORMS MADE THEREBY

(75) Inventors: Ilan Zalit, Rosh-Haain (IL); Fanny Leska, Herzlia (IL); Mali Kadosh, Kfar Saba (IL); Dorit Marco, Nahariya (IL); Yonit Messer-Triger, Tel-Mond (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 487 days.

This patent is subject to a terminal disclaimer.

(21) Appl. No.: 11/481,962

(22) Filed: Jul. 7, 2006

(65) Prior Publication Data

US 2006/0251718 A1    Nov. 9, 2006

Related U.S. Application Data

(63) Continuation of application No. 10/986,494, filed on Nov. 10, 2004.

(51) Int. Cl.
*A61K 9/20*        (2006.01)
*A61K 31/66*       (2006.01)

(52) U.S. Cl. .......................... 424/464; 424/489; 514/102

(58) Field of Classification Search .................. 424/464, 424/489
See application file for complete search history.

(56) References Cited

U.S. PATENT DOCUMENTS

| | | | |
|---|---|---|---|
| 4,551,177 A * | 11/1985 | Trubiano et al. | 106/206.1 |
| 5,393,763 A | 2/1995 | Black et al. | |
| 5,457,117 A | 10/1995 | Black et al. | |
| 5,478,847 A | 12/1995 | Draper | |
| 5,811,120 A | 9/1998 | Gibson et al. | |
| 5,972,383 A | 10/1999 | Gibson et al. | |
| 6,458,811 B1 | 10/2002 | Arbuthnot et al. | |
| 6,797,719 B2 | 9/2004 | Arbuthnot et al. | |
| 6,894,064 B2 | 5/2005 | Arbuthnot et al. | |
| 6,906,086 B2 | 6/2005 | Black | |
| RE38,968 E | 2/2006 | Black et al. | |
| RE39,049 E | 3/2006 | Black et al. | |
| RE39,050 E | 3/2006 | Black et al. | |
| 2004/0186105 A1 | 9/2004 | Allenspach et al. | |

(Continued)

FOREIGN PATENT DOCUMENTS

| | | |
|---|---|---|
| CA | 2372025 | 11/2000 |
| EP | 0674 903 | 10/1995 |

(Continued)

OTHER PUBLICATIONS

Shangraw. Pharmaceutical dosage forms- Tablets, vol. 2, Chapter 4, paes 195-205. ed. Liberman et al. 1990.*

(Continued)

*Primary Examiner* — Lakshmi Channavajjala
(74) *Attorney, Agent, or Firm* — Kenyon & Kenyon LLP

(57) ABSTRACT

A pharmaceutical formulation of compounds with low aqueous solubility and method of manufacture thereof. The formulation may include a pharmacologically active compound having low aqueous solubility and starch in the amount of greater than about 25 weight percent. A manufacturing method may include blending the active compound and starch, compressing the blend into a solid, comminuting the solid into granules, wetting the granules, drying the granules, and tabletting the dried granules to make a solid pharmaceutical formulation.

21 Claims, 2 Drawing Sheets

U.S. PATENT DOCUMENTS

| | | | |
|---|---|---|---|
| 2006/0099252 A1* | 5/2006 | Zalit et al. | 424/464 |
| 2007/0100147 A1 | 5/2007 | Ferrari et al. | |

FOREIGN PATENT DOCUMENTS

| | | |
|---|---|---|
| EP | 1 438 957 | 7/2004 |
| JP | 10-310525 | 11/1998 |
| JP | 11512736 | 11/1999 |
| JP | 2000-511935 | 9/2000 |
| JP | 2003535885 | 12/2003 |
| JP | 2004-529966 | 9/2004 |
| JP | 2004-292459 | 10/2004 |
| WO | 96/26726 | 9/1996 |
| WO | WO97/12583 | 4/1997 |
| WO | 9835681 | 8/1998 |
| WO | WO01/97782 | 12/2001 |
| WO | WO 02/03987 | 1/2002 |
| WO | 02094774 | 11/2002 |
| WO | 03011283 A1 | 2/2003 |
| WO | WO 2004/066910 | 8/2004 |
| WO | 2005/003116 A1 | 1/2005 |
| WO | WO 2005/000296 | 1/2005 |

OTHER PUBLICATIONS

Remington: The Science and Practice of Pharmacy, 20th ed., A. R. Gennaro Ed., Lippincott Williams & Wilkins, 2000, pp. 656, 657.
G. Levy, Gumtow RH. "Effect of certain formulation factors on dissolution rate of the active ingredient III: tablet lubricants", *J Pharm Sci*, 1963, 52, pp. 1139-1144.
P. Finholt, "Effect of Different Factors on Dissolution Rate of Drugs from Powders, Granules and Tablets II", Meddelelser Norsk Farmaceutisk Selskap, 1966, 28, pp. 238-252.
R. C. Rowe, Handbook of Pharmaceutical Excipients, 4th Ed., Pharmaceutical Press, 2003, pp. 603-608.
United States Pharmacopeia and National Formulary, 24/19, U.S. Pharmacopeial Convention, 2000, p. 2235.
United States Pharmaceopeia & National Formulary, 26/21, U.S. Pharmacopeial Convention, 2003, p. 2843.
G. Levy et al., "Effect of certain formulation factors on dissolution rate of the active ingredient II", J Pharm Sci, 1963, 52, pp. 1047-1051.
Wierik et al., "A new generation starch product as excipient in pharmaceutical tablets III. Parameters affecting controlled drug release from tablets based on high surface area retrograded pregelatinized potato starch", International Journal of Pharmaceutics, 157: 181-187 (1997).
Kato et al., "Rapidly Disintegrating Tablets Prepared by a Surface-Modifying Method—Comparison of Disintegrants", J. Pharm. Sci. Technol, 62: 87-94 (2002).
Nakai et al., "Relationship between Configuration of Starch Grains in Tablet and Tablet Disintegration", Yakugaku Zasshi, 97 (11): 1168-1173 (1977), English Abstract included.
Ringard et al., "Influence de l'etablissement d'un reseau hydrophile et continu d'amidon sur les proprietes des comprimes, III. Essai de determination de la quantite optimale d'agent delitant a utiliser", J. Pharm. Belg., 34(4): 204-211 (1979). English Summary included.

\* cited by examiner

COMPRESSED SOLID DOSAGE FORM MANUFACTURING PROCESS WELL-SUITED FOR USE WITH DRUGS OF LOW AQUEOUS SOLUBILITY AND COMPRESSED SOLID DOSAGE FORMS MADE THEREBY

This application is a continuation of pending application Ser. No. 10/986,494, filed Nov. 10, 2004.

FIELD OF THE INVENTION

This invention relates in general to compressed solid dosage form manufacturing methods and solid dosage forms such as tablets and caplets produced therefrom. The invention relates more particularly to tabletting manufacturing methods and tablets produced therefrom for drugs of low aqueous solubility.

BACKGROUND OF THE INVENTION

When solid dosage forms are taken orally, in many cases, the drug must dissolve in aqueous gastrointestinal fluids in, e.g., the patient's stomach before the drug can exert a therapeutic effect. A recurring problem with compressed solid oral dosage forms, such as tablets and caplets (i.e., capsule-shaped tablets) is that the rate of dissolution of some drugs from the dosage form limits their biological availability. This problem arises from the fact that many drugs are small organic molecules with low solubility in aqueous fluids. There are several ways to address the solubility problem of poorly soluble drugs.

For example, the drug itself can be modified. The physical form of the drug can be manipulated by various techniques to optimize the rate at which the drug dissolves. Of these techniques, the one most relevant to the present invention is particle size reduction. The rate of dissolution of a solid may often depend upon the surface area that is exposed to the dissolving medium and since the surface area of a given mass of a substance is generally inversely proportional to the substance's particle size, reducing the particle size of a powder or granular substance may increase its dissolution rate.

Where it is effective, particle size reduction increases the dissolution rate of a particulate solid by increasing the surface area that is exposed to the dissolving medium. However, particle size reduction is not always effective at increasing the dissolution rate of a drug from a compressed solid dosage form. Many hydrophobic drugs have a strong tendency to agglomerate during the dosage form manufacturing process into larger particles with an overall decrease in effective surface area. *Remington: The Science and Practice of Pharmacy*, 20th ed. 656, 657 (A. R. Gennaro Ed., Lippincott Williams & Wilkins: Philadelphia 2000), incorporated by reference herein, contains a more thorough discussion of the concept of "effective surface area" and the effect of particle size on dissolution. A drug that has ostensibly been milled to a fine particle size will sometimes display dissolution characteristics of a larger particle due to agglomeration or similar effect.

There are three well known processes for manufacturing compressed solid dosage forms: the wet granulation method, the double-compression method (also known as dry granulation) and the direct compression method. In each of these methods, there are blending steps which can promote agglomeration of fine particles of the drug into larger, less rapidly dissolving, particles.

In the wet granulation method, pre-weighed drug and one or more other ingredients, like a diluent, are blended. The blend is then mixed with a liquid such as water or ethanol which causes the particles to agglomerate into a damp mass. Sometimes the liquid contains a binder. The damp mass is screened to produce granules which are then dried. The dry granules are screened to produce granules of a predetermined size. Then, the granules are typically blended with a solid lubricant and possibly other ingredients. Lastly, the lubricated granules and any other extra-granular ingredients are compressed into a tablet, which may subsequently be coated.

The double-compression or dry granulation method has fewer steps than wet granulation and does not require contact with a liquid or drying, which makes it well suited for formulating water sensitive and heat sensitive drugs. In the double-compression method, the drug and other ingredients, such as a lubricant, are blended and then compressed in a first compression step. There are two conventional first compression techniques. One is roller compaction where the blend is fed between rollers which press it into sheets and the other is slugging where the blend is compressed into slugs, which are tablet-like forms that are typically larger than tablets intended for human consumption. The resulting sheets or slugs are then comminuted into granules, mixed with a solid lubricant and compressed in a second compression step to produce the final tablet.

The direct compression method is the simplest of the three well known methods for making compressed solid dosage forms. In the direct compression method, the drug and any other ingredients are blended together and directly compressed into the final tablet. The tablet ingredients must have good flow properties and cohesion to be suitable for direct compression tabletting. Microcrystalline cellulose and lactose are two commonly used diluents in direct compression tabletting.

U.S. Pat. No. 6,458,811, incorporated by reference herein in its entirety, describes a pharmaceutical formulation comprising raloxifene in particulate form, said particles having a mean particle size of between about 5 and about 20 microns, at least about 90% of said particles having a size of less than about 35 microns.

In addition to modifying the physical characteristics of the drug, the composition of the dosage form can be adjusted to promote dissolution of the drug. For example, U.S. Pat. No. 5,972,383, incorporated by reference herein in its entirety, describes an orally administrable pharmaceutical formulation comprising raloxifene and a hydrophilic carrier composition. The hydrophilic carrier composition contains a surfactant, a water-soluble diluent, and a hydrophilic binder.

Our experimental work has been guided by a search for ways to modify the composition and method of manufacturing of oral dosage forms to promote dissolution of poorly soluble drugs. Our experimental work also focused on the search for novel manufacturing processes and compositions which enable us to utilize larger drug particles than recommended in the literature, while maintaining a fast dissolution rate and concomitant high bioavailability. The drug raloxifene has been used as a model in much of this work. However, it its more general application, the invention disclosed herein is not to be construed as limited to raloxifene solid dosage forms.

In a well known study published in 1963, Levy et al. reported on the effect of starch on the rate of dissolution of salicylic acid from tablets manufactured by double compression. Levy, G. et al., *J. Pharm. Sci.* 1963, 52, 1047. It was discovered that increasing the starch content from 5 to 20% increased the rate of dissolution of salicylic acid three fold. This observation was attributed to faster disintegration of tablets with a higher starch content. In 1967, Finholt et al. observed that fine starch particles added to phenobarbital tablets increased the dissolution rate of phenobarbital from the tablets. Reaching a different conclusion from Levy et al., it was proposed that the starch worked by coating the phenobarbital crystals and imparting a hydrophilic property to them, which improved contact between the phenobarbital particles and an aqueous dissolution medium. Finholt, P. *Medd Norsk Farm. Selsk.* 1966, 28, 238.

Starch is a common ingredient of tablets, where it is used for a variety of purposes. It is routinely used, e.g., as a diluent, binder, disintegrant, and glidant. Diluents increase the bulk of a solid pharmaceutical composition and can make a pharmaceutical dosage form containing the composition easier for the patient and caregiver to handle. Binders help bind the active ingredient and other ingredients together, for example, during granulation or compression steps. Disintegrants accelerate break up of the tablet in a patient's stomach, typically by drawing water into the tablet and causing it to swell, thereby breaking the tablet into smaller pieces (resulting in greater surface area). Glidants improve the flowability of powder compositions by coating the surfaces of the particles. According to the *Handbook of Pharmaceutical Excipients* 4th Ed. 603-604. (Pharmaceutical Press: London 2003), incorporated by reference herein in its entirety, starch is commonly used in an amount of 5-15% when it functions as a binder. (All percentages, unless otherwise specified, are percentage by weight based on the total weight of the compressed solid dosage form.) When functioning as a disintegrant, it is commonly added in an amount of 3-15%. Id. The amount of diluent that is called for in a particular application depends upon many parameters and is highly variable. However, as the *Handbook* notes, starch does not compress well and tends to increase tablet friability and capping if used in high concentrations. Id. Thus, the use of high concentrations of starch as a diluent is limited by the deterioration in the hardness and friability (resistance to chipping) that occurs as the proportion of starch in the formulation is increased.

It would be highly desirable, therefore, to produce a compressed solid dosage form for oral administration having a high rate of dissolution of a poorly soluble drug without having to reduce the particle size of the drug beyond that size which is predicted by surface area calculation due to agglomeration effects.

SUMMARY OF THE INVENTION

In one embodiment, the invention is directed to a compressed solid pharmaceutical dosage form comprising (a) a pharmacologically active compound having low aqueous solubility (e.g., raloxifene) with a particle size distribution such that $d_{(0.5)}$ greater than about 35 µm and $d_{(0.9)}$ less than about 100 µm; and (b) starch in an amount of from about 25 to about 90 weight percent, preferably, from about 35 to about 80 weight percent and, most preferably, from about 45 to about 75 weight percent. The starch may increase the effective surface area of the formulation and, hence, its dissolution rate and bioavailability.

In another embodiment, the invention is directed to a process for preparing a solid pharmaceutical dosage form for a drug having low aqueous solubility that displays an acceptable dissolution rate and more preferably displays a high rate of dissolution. It is understood that for raloxifene tablets, an "acceptable dissolution rate" is exemplified by the release of at least about 60 percent of the labeled dose within about 45 minutes when tested in 900 mL of a 0.1% aqueous polysorbate 80 solution, using paddle apparatus (USP Apparatus II) at 50 rpm, 37° C. When tested in 2 L of the solution, the release of at least about 60 percent of the labeled dose is within about 40 minutes. It is also understood that for raloxifene tablets, a "high rate of dissolution" is exemplified by the release of at least about 50 percent of the labeled dose within about 20 minutes, when tested in 900 mL of a 0.1% aqueous polysorbate 80 solution, using paddle apparatus (USP Apparatus II) at 50 rpm, 37° C. When tested in 2 L of the solution, the release of at least 70 percent of the labeled dose is within about 50 minutes. The process comprises (a) blending a particulate pharmacologically active compound and starch; (b) compressing the blend into a coherent solid; (c) comminuting the coherent solid into granules; (d) wetting the granules with a liquid; (e) drying the wetted granules to form dried granules; and (f) tabletting the dried granules.

In a further embodiment, the invention is directed to a composition and processes for preparing a solid pharmaceutical dosage form of raloxifene that displays an improved dissolution rate and having a particle size distribution significantly larger than that taught by the prior art.

In yet another embodiment, the invention is directed to methods of treating disease, e.g., osteoporosis, comprising orally administering to a patient a compressed pharmaceutical dosage form of the present invention.

These and other embodiments of the present invention are described more fully below.

BRIEF DESCRIPTION OF THE DRAWINGS

FIG. 1 is a plot comparing the percent dissolution of raloxifene over time for:

(1) a raloxifene tablet containing conventional fillers and no starch, made by wet granulation;

(2) a raloxifene tablet with a relatively low starch content (24%), made by wet double compression method;

(3) a raloxifene tablet with a high starch content (64.4%), made by dry granulation; and (4) a raloxifene tablet with a high starch content (60.8%), made by wet double compression method.

The dissolution profile was generated by testing in 900 mL of a 0.1% aqueous polysorbate 80 solution, using paddle apparatus (USP Apparatus II), 50 rpm, 37° C. at 10, 20, 30 and 45 min time points.

Figure 2:
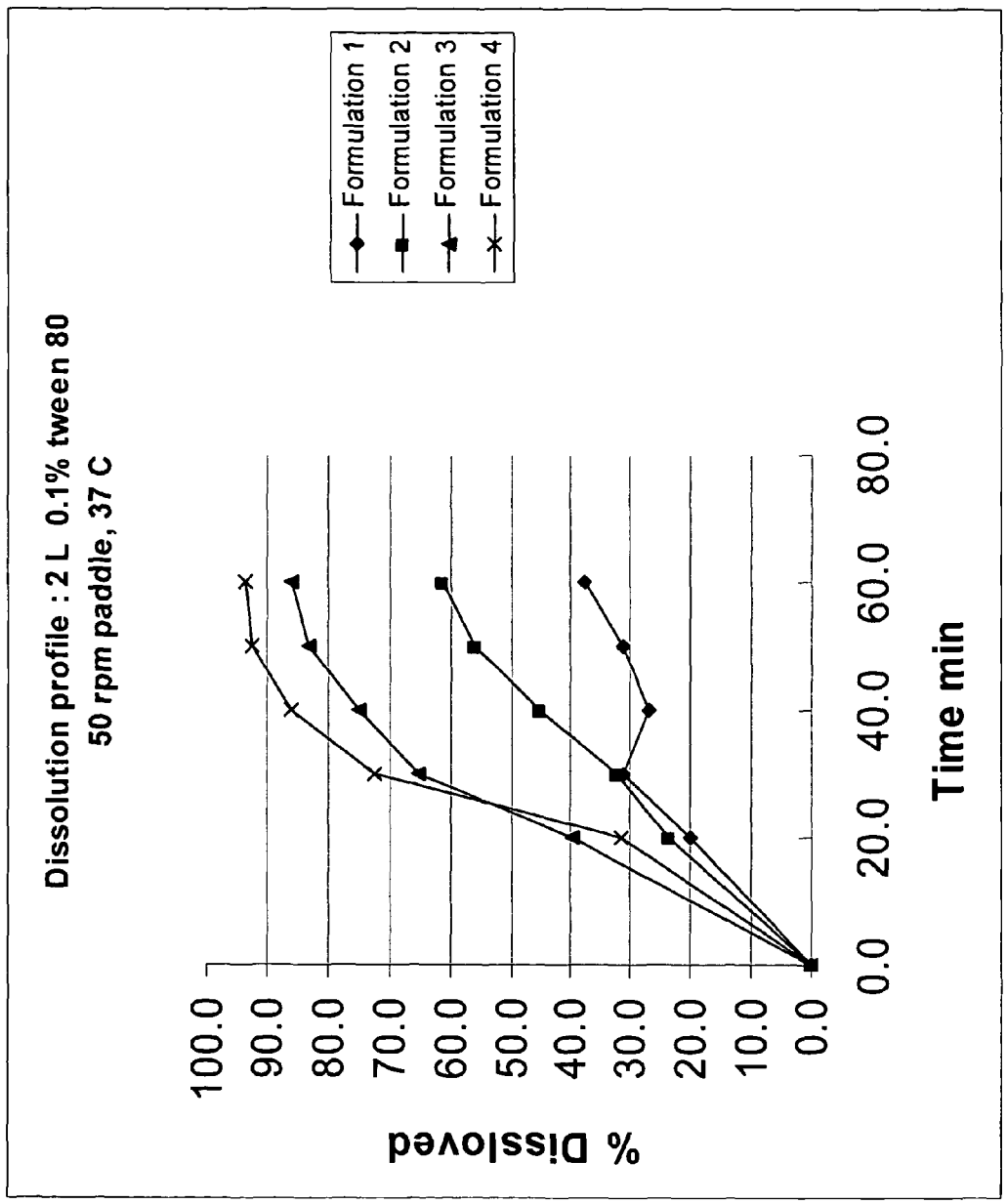

FIG. 2 is a plot comparing the percent dissolution of raloxifene over time for:

(1) a raloxifene tablet containing conventional fillers and no starch, made by wet granulation;

(2) a raloxifene tablet with a relatively low starch content (24%), made by wet double compression method;

(3) a raloxifene tablet with a high starch content (64.4%), made by dry granulation; and (4) a raloxifene tablet with a high starch content (60.8%), made by wet double compression method.

The dissolution profile was generated by testing in 2 L of a 0.1% aqueous polysorbate 80 solution, using paddle apparatus (USP Apparatus II), 50 rpm, 37° C. at 20, 30, 40, 50 and 60 min time points.

DETAILED DESCRIPTION OF THE PREFERRED EMBODIMENTS

In one aspect, the present invention provides a novel process for manufacturing a compressed solid dosage form, such as a tablet. Hereafter, the manufacturing process is referred to as the "wet double compression method." The wet double compression method is advantageously used to make compressed solid dosage forms with a high content of a finely divided hydrophilic material, preferably starch, for administering a drug having low aqueous solubility.

A drug has "low aqueous solubility" or is "poorly soluble" (used interchangeably) if its intrinsic water solubility (i.e., water solubility of the un-ionized form) is less than about 1% by weight, and typically less than about 0.1% or 0.01% by weight. Such drugs include, but are not limited to, raloxifene, oxcarbazepine and atorvastatin. pharmaceutically acceptable salts, isomers and derivatives thereof, and mixtures thereof.

The term "gastric fluid" means the endogenous fluid medium of the stomach, including water and secretions. "Simulated gastric fluid" means any fluid that is generally recognized as providing a useful substitute for authentic gastric fluid in experiments designed to assess the dissolution rate of substances in the stomach. One such simulated gastric fluid is USP Gastric Fluid TS, without enzymes. *United States Pharmacopeia and National Formulary* 24/19 p. 2235 (1999).

Several hydrophilic materials can be used in the manufacturing process. We have found that a relatively high concentration of starch in the composition has marked effect on improving the dissolution rate of the final dosage form. Thus, the preferred hydrophilic excipient is starch. Starch is a naturally occurring polysaccharide that is derived from several different plant sources, including corn, potatoes, tapioca, rice and wheat. It is composed of amylose and amylopectin units. Starch is commercially available from numerous manufacturers such as Anheuser Busch, Starchem, AE Staley Mfg. Co., Matheson, Coleman & Bell and Henkel Corp. A preferred starch for use in the present invention is pregelatinized starch meeting the requirements of the Official Monograph of the National Formulary. *United States Pharmaceopeia & National Formulary* 26/21 2843 (U.S. Pharmacopeial Convention, Inc.: Rockville, Md. 2003).

The improvement in dissolution rate achieved may occur by various mechanisms. While not intending to be bound by any particular theory as to how the relatively high concentrations of excipients, exemplified by starch, increases the rate of dissolution of a poorly soluble drug, the particle size of the starch is not believed to be critical.

The preferred wet double compression process comprises six steps. In the first step, a pharmacologically active compound in particulate form is blended with powdered hydrophilic material, preferably starch, to produce a homogenous blend. The quantity of the pharmacologically active compound and hydrophilic material to be blended will be determined taking into consideration the ratio of ingredients, potency and size of the final compressed dosage form. However, when the active pharmaceutical ingredient is poorly soluble in both naturally occurring and simulated gastric and/or intestinal fluids, the amount of hydrophilic material is preferably provided in an amount that will result in the hydrophilic material comprising from about 25 to about 90 weight percent (wt. %), preferably, from about 35 to about 80 wt. %, and, most preferably, from about 45 to about 75 wt. % of the final dosage form.

In addition to the active compound and hydrophilic material, other ingredients may also be blended at this stage. Blending can be performed by any known method and using any equipment capable of producing a homogeneous powder mixture, such as a V-cone blender, powder mixer, high shear mixer, or fluidized bed granulator.

In the second step, the blend is compressed into a coherent solid. This may be done using conventional dry granulation techniques like slugging and roller compaction, which produce slugs, ribbons or sheets.

In the third step, the coherent solid is comminuted into granules. Comminution may be performed with a mill such as a Fitzpatrick mill or by screening.

In the fourth step, the granules are wetted with a liquid. Preferred liquids are water and $C_1$-$C_4$ alcohols, with ethanol being especially preferred. Yet more preferably, the liquid is a solution of a binder in water or a $C_1$-$C_4$ alcohol. Suitable binders include, for example, polyvinylpyrrolidone (povidone), polyethylene glycol, sugars, invert sugars, poloxamers (PLURONIC® F68, PLURONIC® F127), collagen, albumin, celluloses in nonaqueous solvents, poly(propylene glycol), polyoxyethylene-polypropylene copolymer, polyethylene ester, polyethylene sorbitan ester, poly(ethylene oxide), microcrystalline cellulose. A particularly preferred binder is PVP K-30. Guidance as to the quantity of liquid to use and the type and quantity of additional ingredients that may be added during this wetting step can be obtained by reference to the known conditions employed in conventional wet granulating processes. Accordingly, enough of the liquid is used so that the granules and any other solid ingredients included in this step will be thoroughly wetted, yet not so much that there is a significant amount of free-flowing liquid remaining after all of the insoluble ingredients have been added. Suitable fillers that may be added include, e.g., dibasic calcium phosphate, kaolin, sucrose, mannitol, microcrystalline cellulose, powdered cellulose, precipitated calcium carbonate, sorbitol, starch, lactose and combinations thereof. Further, additional solid ingredients that may be added include an acidifying agent, alkalizing agent, adsorbent, antioxidant, buffering agent, colorant, electrolyte, emulsifying (suspending) agent, flavorant, fragrance, sweetening agent, antiadherent, binder, diluent, excipient, disintegrant, glidant, lubricant, opaquant, and/or polishing agent.

In the fifth step of the manufacturing process, the wetted granules are dried. Drying can be performed using any conventional drying equipment such as a tray dryer or a fluid bed dryer. The drying temperature will dependent in part upon the thermolability of the active ingredient.

Optionally, additional excipients may be mixed with the dried granules. For instance, it may be necessary or desirable to add a glidant and/or a lubricant before loading the granules into the feed hopper of a tabletting machine.

In the sixth step of the process, the optionally lubricated dried granules and any other optional extragranular ingredients are compressed into a solid dosage form. Any conventional tabletting machinery may be used, such as a hand-operated press, a single station tabletting press or a rotary tabletting press. The operation of such machinery is well within the ordinary skill in the art.

After tabletting, the tablets may optionally be coated. The coated or uncoated tablets are packaged in conventional manner with appropriate labeling instructing doctors and patients on the proper use of the tablets.

In another aspect, the present invention provides compressed solid dosage forms containing a pharmacologically active compound having low aqueous solubility and from about 25 to about 80 wt. % starch. The compressed solid dosage forms of this invention are resilient to impact.

The resiliency of tablets toward impact is quantitated in the pharmaceutical industry by the tablet's hardness and friability. Tablet hardness is a measure of the tablet's propensity to fracture under applied pressure. Devices for measuring hardness are commercially available from a variety of manufacturers such as KRAEMER (UTS) Ltd. Compressed solid dosage forms of this invention have a hardness of at least about 5 Strong-Cobb units when measured using a KRAEMER (UTS). Friability is measured using the USP testing method. Compressed solid dosage forms of this invention have a friability of less than about 1%, preferably less than about 1%.

In accordance with the present invention, drugs with low aqueous solubility may be used in treating disease by orally administering such drugs in the dosage forms of the invention. For example, the formulations may be used in a method of treating osteoporosis, in particular. The following formulation examples are illustrative only and are not intended to limit the scope of the invention in any way.

EXAMPLES

General

The starch used in these examples was pregelatinized starch, available from Colorcon. The microcrystalline cellulose used was Avicel® PH 102, available from FMC Biopolymer. The lactose monohydrate used is available from DMV. The magnesium stearate used is available from Peter Greven. The crospovidone used is available from ISP Technologies Inc. The colloidal silicon dioxide used was Aerosil® 200, available from Degussa.

Analysis of the raloxifene hydrochloride used showed that the particle size distribution met the following specifications: $d_{(0.5)}$ greater than about 35 µm, $d_{(0.9)}$ less than about 100 µm. For example, in Formulations 1-4 below, $d_{(0.5)}$=38.8 µm and $d_{(0.9)}$=90.4 µm. All particle sizes herein refer to the mean equivalent spherical diameter measured by laser light scattering techniques. Thus, the notation "$d_{(0.5)}$ greater than about 35 µm" means that 50% of the particles by volume have a mean equivalent spherical diameter of more than about 35 µm, as measured by laser light scattering. The laser light scattering measurement instrument used to measure the particle size distributions in the Examples was a Malvern Mastersizer® S. The dissolution profile was generated by testing in either 900 mL or 2 L of a 0.1% aqueous polysorbate 80 solution, using paddle apparatus (USP Apparatus II) at 50 rpm at 37° C.

Example 1

Formulation 1 (Comparative)

A raloxifene hydrochloride tablet having conventional fillers was made by wet granulation. The ingredients in Table 1 were wet granulated and then compressed into tablets weighing 250 mg. Starch was not used in Formulation 1. Microcrystalline cellulose and lactose, two commonly used fillers, were used instead of starch. The dissolution profile of Formulation 1 in 900 mL and 2 L of 0.1% aqueous polysorbate 80 solution, paddle (Apparatus II) at 50 rpm was tested (see dissolution rate study, below).

TABLE 1

| Ingredient | Weight (mg/tablet) | Weight Percent |
|---|---|---|
| Part I | | |
| Raloxifene hydrochloride | 60 | 24% |
| Crospovidone | 10 | 4% |
| Microcrystalline cellulose | 76.5 | 30.6% |
| Part II | | |
| Lactose monohydrate | 100 | 40% |

TABLE 1-continued

| Ingredient | Weight (mg/tablet) | Weight Percent |
|---|---|---|
| Part III | | |
| Colloidal silicon dioxide | 1 | 0.4% |
| Part IV | | |
| Magnesium stearate | 2.5 | 1% |

1. Part I ingredients were thoroughly blended.
2. Blend of part I was granulated by adding granulation solution (lactose of part II dissolved in water), the granules were dried and milled (0.6 mm sieve).
3. The Part III ingredient was then blended with the granules for about 15 minutes.
4. The Part IV ingredient was then blended with the granules for about 5 minutes.
5. The lubricated granules were compressed into tablets 12.0 × 5.5 mm. Tablet hardness was found to be 9 Strong-Cobb units.

Example 2

Formulation 2 (Comparative)

Raloxifene tablets weighing 250 mg were made from the ingredients listed in Table 2 by the wet double compression method. Formulation 2 is an example of use of a relatively low starch content from about 0 up to about 24 wt. %. The dissolution profile of Formulation 2 in 900 mL and 2 L of 0.1% aqueous polysorbate 80 solution, paddle (Apparatus II) at 50 rpm was tested (see dissolution rate study, below).

TABLE 2

| Ingredient | Weight (mg/tablet) | Weight Percent |
|---|---|---|
| Part I | | |
| Raloxifene hydrochloride | 60 | 24% |
| Starch | 60 | 24% |
| Part II | | |
| Magnesium stearate | 2 | 0.8% |
| Part III | | |
| Microcrystalline cellulose | 85 | 34% |
| Polyvinylpyrrolidinone | 9 | 3.6% |
| Part IV | | |
| Microcrystalline cellulose | 30.75 | 12.3% |
| Colloidal silicon dioxide | 1.25 | 0.5% |
| Part V | | |
| Magnesium stearate | 2 | 0.8% |

1. Part I ingredients were thoroughly blended.
2. Part II ingredient was added to part I and blended, and compressed into slugs.
3. The slugs were then milled into granules.
4. Granules obtained after step 3 with addition of microcrystalline cellulose (Part III) were granulated in a granulation solution (PVP dissolved in EtOH 95%). The granules were dried and milled (0.6 mm sieve).
5. The Part IV ingredients were then blended with the granules for about 15 minutes.
6. The Part V ingredient was then blended with the granules for about 5 minutes.
7. The resultant blend was compressed into tablets 12.0 × 5.5 mm. Tablet hardness was found to be about 9 to 10 Strong-Cobb units.

Example 3

Preparative

Formulation 3

Raloxifene tablets weighing 250 mg were made from the ingredients listed in Table 3 utilizing a dry granulation method. Formulation 3 is an example of use of a high starch content from about 35 to about 75 wt. %. The dissolution profile of Formulation 3 in 900 mL and 2 L of 0.1% aqueous polysorbate 80 solution, paddle (Apparatus II) at 50 rpm was tested (see dissolution rate study, below).

TABLE 3

| Ingredient | Weight (mg/tablet) | Weight Percent |
|---|---|---|
| Part I | | |
| Raloxifene hydrochloride | 60 | 24% |
| Starch | 161 | 64.4% |
| Part II | | |
| Magnesium stearate | 0.75 | 0.3% |
| Part III | | |
| Microcrystalline cellulose | 25.25 | 10.1% |
| Colloidal silicon dioxide | 1.25 | 0.5% |
| Part IV | | |
| Magnesium stearate | 1.75 | 0.7% |

1. Part I ingredients were thoroughly blended.
2. Part II ingredient was added to part I and blended, and compressed into slugs.
3. The slugs were then milled into granules.
4. The Part III ingredients were then blended with the granules for about 15 minutes.
5. The Part IV ingredient was then blended with the granules for about 5 minutes.
6. The resultant blend was compressed into tablets 12.0 × 5.5 mm. Tablet hardness was found to be about 11 Strong-Cobb units.

Formulation 4

Raloxifene tablets weighing 250 mg were made from the ingredients listed in Table 4 by the wet double compression method. The dissolution profile of Formulation 4 in 900 mL and 2 L of 0.1% aqueous polysorbate 80 solution, paddle (Apparatus II) at 50 rpm was tested (see dissolution rate study, below).

TABLE 4

| Ingredient | Weight (mg/tablet) | Weight Percent |
|---|---|---|
| Part I | | |
| Raloxifene hydrochloride | 60 | 24% |
| Starch | 152 | 60.8% |
| Part II | | |
| Magnesium stearate | 0.75 | 0.3% |
| Part III | | |
| Polyvinylpyrrolidinone | 9 | 3.6% |
| Part IV | | |
| Microcrystalline cellulose | 25.25 | 10.1% |
| Colloidal silicon dioxide | 1.25 | 0.5% |
| Part V | | |
| Magnesium stearate | 1.75 | 0.7% |

1. Part I ingredients were thoroughly blended.
2. Part II ingredient was added to part I and blended, and compressed into slugs.
3. The slugs were then milled into granules.
4. Granules obtained after step 3 were further granulated in a granulation solution (PVP dissolved in EtOH 95%). The granules were dried and milled (0.6 mm sieve).
5. The Part IV ingredients were then blended with the granules for about 15 minutes.
6. The Part V ingredient was then blended with the granules for about 5 minutes.
7. The resultant blend was compressed into tablets 12.0 × 5.5 mm. Tablet hardness was found to be about 7 Strong-Cobb units.

Formulation 5

Raloxifene tablets weighing 350 mg are made from the ingredients listed in Table 5 by the wet double compression method. Formulation 5 is an example of use of a very high starch content above about 75 wt. %.

TABLE 5

| Ingredient | Weight (mg/tablet) | Weight Percent |
|---|---|---|
| Part I | | |
| Raloxifene hydrochloride | 60 | 24% |
| Starch | 262.5 | 75% |
| Part II | | |
| Magnesium stearate | 1 | 0.28% |
| Part III | | |
| Polyvinylpyrrolidinone | 9 | 2.57% |
| Part IV | | |
| Microcrystalline cellulose | 14.5 | 4.14% |
| Colloidal silicon dioxide | 1.0 | 0.28% |
| Part V | | |
| Magnesium stearate | 2 | 0.56% |

1. Part I ingredients are thoroughly blended.
2. Part II ingredient is added to part I and blended, and compressed into slugs.
3. The slugs are then milled into granules.
4. Granules obtained after 3 are granulated in a granulation solution (PVP dissolved in EtOH 95%). The granules are dried and milled (0.6 mm sieve).
5. The Part IV ingredients are then blended with the granules for about 15 minutes.
6. The Part V ingredient is then blended with the granules for about 5 minutes.
7. The resultant blend is compressed into tablets 12.0 × 5.5 mm. Tablet hardness is expected to be about more than 5 Strong-Cobb units.

Dissolution Rate Study

Figure 1:
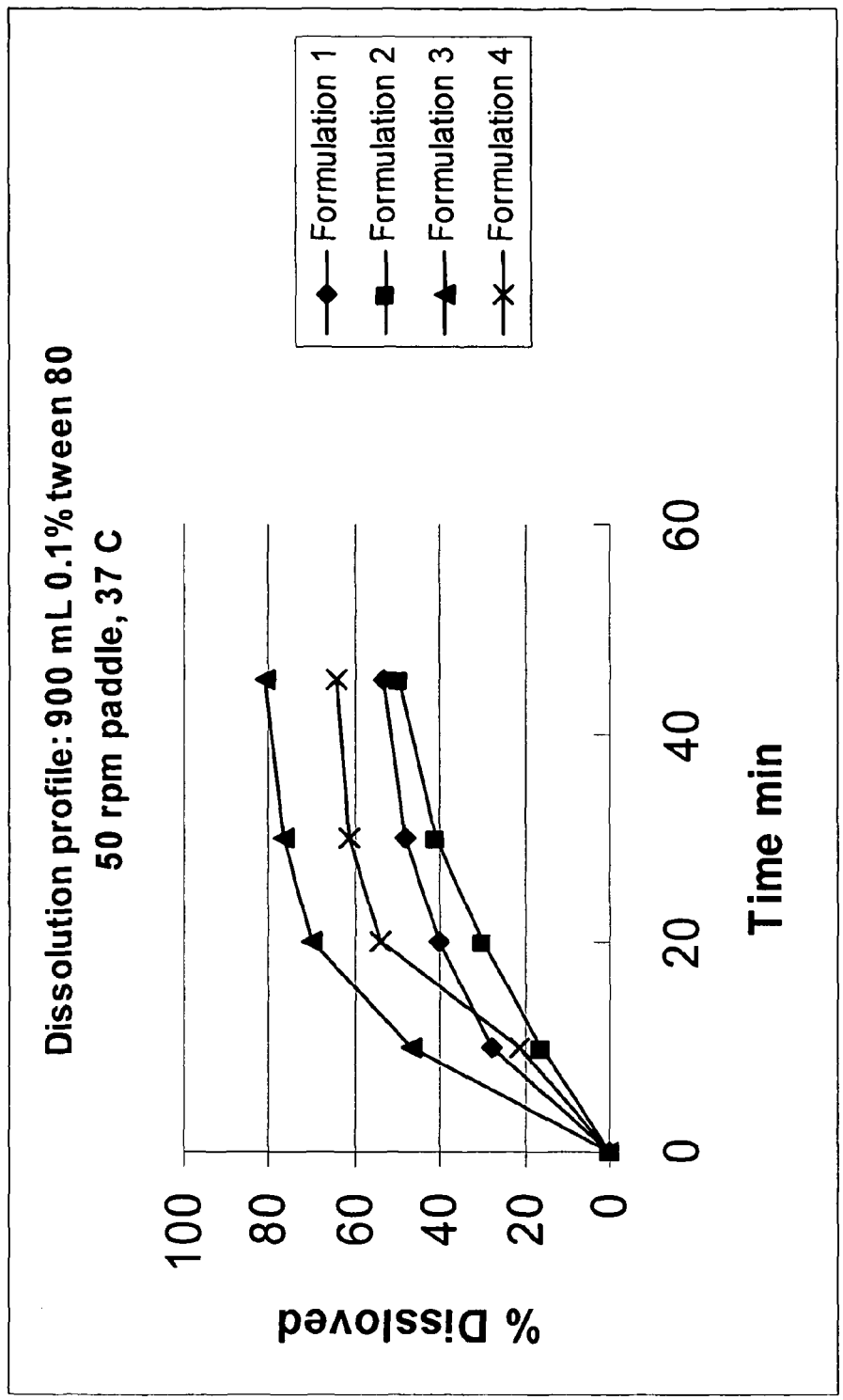

The dissolution rates of Formulations 1-4 were tested in 900 mL of a 0.1% aqueous polysorbate 80 solution, paddle apparatus (USP Apparatus II, 50 rpm, 37° C.) at 10, 20, 30 and 45 min intervals. The dissolution data are shown in Table 6 and the dissolution profile is shown in FIG. 1. The dissolution rates of Formulations 1-4 were also tested in 2 L of a 0.1% aqueous polysorbate 80 solution, paddle apparatus (USP Apparatus II, 50 rpm, 37° C.) at 20, 30, 40, 50 and 60 min intervals. The dissolution data are shown in Table 7 and the dissolution profile is shown in FIG. 2.

Results

TABLE 6

(900 mL of a 0.1% aqueous polysorbate 80 solution)

| time min | no starch Formulation 1 | 24% starch (wet double compression) Formulation 2 | 64% starch (double compression) Formulation 3 | 60.8% starch (wet double compression) Formulation 4 |
|---|---|---|---|---|
| 0 | 0 | 0 | 0 | 0 |
| 10 | 28 | 16 | 47 | 21 |
| 20 | 40 | 30 | 70 | 54 |
| 30 | 48 | 41 | 77 | 61 |
| 45 | 53 | 50 | 81 | 64 |

TABLE 7

(2 L of a 0.1% aqueous polysorbate 80 solution)

| time min | no starch Formulation 1 | 24% starch (wet double compression) formulation 2 | 64% starch (double compression) Formulation 3 | 60.8% starch (wet double compression) Formulation 4 |
|---|---|---|---|---|
| 0 | 0 | 0 | 0 | 0 |
| 20 | 20.1 | 23.7 | 39.9 | 31.4 |
| 30 | 31.3 | 32.3 | 65.2 | 72.3 |

TABLE 7-continued (2 L of a 0.1% aqueous polysorbate 80 solution)

| time min | no starch Formulation 1 | 24% starch (wet double compression) formulation 2 | 64% starch (double compression) Formulation 3 | 60.8% starch (wet double compression) Formulation 4 |
|---|---|---|---|---|
| 40 | 26.8 | 45.2 | 75.0 | 86.0 |
| 50 | 31.2 | 56.0 | 83.2 | 92.6 |
| 60 | 37.6 | 61.2 | 85.9 | 93.6 |

As can be seen in FIG. 1 and FIG. 2, the use of high level of starch as a filler in Formulations 3 and 4 greatly increased the dissolution rate of the raloxifene relative to Formulation 1, which used conventional direct compression fillers, and relative to Formulation 2, which used a relatively low level of starch.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

What is claimed is:

1. A compressed pharmaceutical dosage form comprising:
   a) raloxifene hydrochloride, and
   b) starch in an amount of greater than 25 weight percent of the dosage form, wherein the raloxifene hydrochloride has a particle size distribution such that $d_{(50)}$ is greater than or equal to 35 μm and $d_{(90)}$ is less than or equal to 100 μm, as measured by laser light scattering.

2. The compressed pharmaceutical dosage form of claim 1 wherein the amount of starch is from 35 to 80 weight percent.

3. The compressed pharmaceutical dosage form of claim 1 having a hardness of 5 or greater than 5 Strong-Cobb units.

4. The compressed pharmaceutical dosage form of claim 2 wherein the amount of starch is from 45 weight percent to 75 weight percent.

5. The compressed pharmaceutical dosage form of claim 1 wherein more than 50% of the raloxifene hydrochloride is dissolved in 20 minutes in 900 mL of a 0.1% aqueous polysorbate 80 solution, USP paddle apparatus at 50 rpm, 37° C.

6. A method of treating osteoporosis comprising orally administering to a patient a compressed pharmaceutical dosage form of claim 1.

7. The compressed pharmaceutical dosage form of claim 1 wherein more than 60% of the raloxifene hydrochloride in the dosage form is dissolved in 45 minutes in 900 mL of a 0.1% aqueous polysorbate 80 solution, USP paddle apparatus at 50 rpm, 37° C.

8. The compressed pharmaceutical dosage form of claim 1 wherein more than 60% of the raloxifene hydrochloride in the dosage form is dissolved in 40 minutes in 2 L of a 0.1% aqueous polysorbate 80 solution, USP paddle apparatus at 50 rpm, 37° C.

9. The compressed pharmaceutical dosage form of claim 1 wherein more than 50% of the raloxifene hydrochloride in the dosage form is dissolved in 20 minutes in 900 mL of a 0.1% aqueous polysorbate 80 solution, USP paddle apparatus at 50 rpm, 37° C.

10. The compressed pharmaceutical dosage form of claim 1 wherein more than 50% of the raloxifene hydrochloride in the dosage form is dissolved in 30 minutes in 2 L of a 0.1% aqueous polysorbate 80 solution, USP paddle apparatus at 50 rpm, 37° C.

11. The compressed pharmaceutical dosage form of claim 1 wherein more than 70% of the raloxifene hydrochloride in the dosage form is dissolved in 50 minutes in 2 L of a 0.1% aqueous polysorbate 80 solution, USP paddle apparatus at 50 rpm, 37° C.

12. A compressed pharmaceutical dosage form comprising raloxifene hydrochloride and a hydrophilic excipient,
    wherein the raloxifene hydrochloride has a particle size distribution such that $d_{(50)}$ is greater than or equal to 35 μm and $d_{(90)}$ is less than or equal to 100 μm, as measured by laser light scattering,
    wherein the hydrophilic excipient is present in an amount such that:
    a) more than 60% of the raloxifene hydrochloride in the dosage form is dissolved in 40 minutes in 2 L of a 0.1% aqueous polysorbate 80 solution, USP paddle apparatus at 50 rpm, 37° C., or
    b) more than 60% of the raloxifene hydrochloride in the dosage form is dissolved in 45 minutes in 900 mL of a 0.1% aqueous polysorbate 80 solution, USP paddle apparatus at 50 rpm, 37° C.

13. The compressed pharmaceutical dosage form of claim 12 wherein more than 60% of the raloxifene hydrochloride in the dosage form is dissolved in 45 minutes in 900 mL of a 0.1% aqueous polysorbate 80 solution, USP paddle apparatus at 50 rpm, 37° C.

14. The compressed pharmaceutical dosage form of claim 12 wherein more than 60% of the raloxifene hydrochloride in the dosage form is dissolved in 40 minutes in 2 L of a 0.1% aqueous polysorbate 80 solution, USP paddle apparatus at 50 rpm, 37° C.

15. The compressed pharmaceutical dosage form of claim 12 wherein more than 50% of the raloxifene hydrochloride in the dosage form is dissolved in 20 minutes in 900 mL of a 0.1% aqueous polysorbate 80 solution, USP paddle apparatus at 50 rpm, 37° C.

16. The compressed pharmaceutical dosage form of claim 12 wherein more than 50% of the raloxifene hydrochloride in the dosage form is dissolved in 30 minutes in 2 L of a 0.1% aqueous polysorbate 80 solution, USP paddle apparatus at 50 rpm, 37° C.

17. The compressed pharmaceutical dosage form of claim 12 wherein more than 70% of the raloxifene hydrochloride is dissolved in 50 minutes in 2 L of a 0.1% aqueous polysorbate 80 solution, USP paddle apparatus at 50 rpm, 37° C.

18. The compressed pharmaceutical dosage form of claim 12 wherein the hydrophilic excipient is present in an amount of between 25 and 90 weight percent of the dosage form.

19. The compressed pharmaceutical dosage form of claim 18 wherein the hydrophilic excipient is starch.

20. The compressed pharmaceutical dosage form of claim 19 wherein the dosage form is a tablet.

21. The compressed pharmaceutical dosage form of claim 1 wherein the dosage form is a tablet.

* * * * *